(12) United States Patent
Doherty et al.

(10) Patent No.: US 7,728,989 B2
(45) Date of Patent: Jun. 1, 2010

(54) DOUBLE-SIDED MEASUREMENT OF DENTAL OBJECTS USING AN OPTICAL SCANNER

(75) Inventors: Michael Doherty, Peabody, MA (US); Yitzhak Daniel, Givat Ze'ev (IL); Eli Zeitlin, Jerusalem (IL); Karol Sanilevici, Jerusalem (IL); Gabriel Y. Sirat, Jerusalem (IL); Gregory Agronik, Jerusalem (IL)

(73) Assignee: Optimet, Optical Metrology Ltd., Jerusalem (IL)

( * ) Notice: Subject to any disclaimer, the term of this patent is extended or adjusted under 35 U.S.C. 154(b) by 299 days.

(21) Appl. No.: 11/829,471

(22) Filed: Jul. 27, 2007

(65) Prior Publication Data
US 2007/0293769 A1 Dec. 20, 2007

Related U.S. Application Data

(63) Continuation-in-part of application No. 11/041,520, filed on Jan. 24, 2005, now Pat. No. 7,375,827.

(60) Provisional application No. 60/544,468, filed on Feb. 13, 2004, provisional application No. 60/834,138, filed on Jul. 28, 2006, provisional application No. 60/920,972, filed on Mar. 30, 2007.

(51) Int. Cl.
*G01B 11/14* (2006.01)
(52) U.S. Cl. .................... 356/614; 356/622
(58) Field of Classification Search ......... 356/601–623; 433/213, 29, 215, 229
See application file for complete search history.

(56) References Cited

U.S. PATENT DOCUMENTS

| | | | |
|---|---|---|---|
| 3,692,414 A | 9/1972 | Hosterman et al. | 356/167 |
| 4,136,949 A | 1/1979 | Hayamizu et al. | 356/1 |
| 4,744,664 A | 5/1988 | Offt et al. | 356/615 |
| 5,338,198 A * | 8/1994 | Wu et al. | 433/213 |
| 6,334,773 B1 * | 1/2002 | Ahlen et al. | 433/29 |

FOREIGN PATENT DOCUMENTS

DE  41 02 404   7/1992

* cited by examiner

*Primary Examiner*—Hoa Q Pham
(74) *Attorney, Agent, or Firm*—Sunstein Kann Murphy & Timbers LLP

(57) ABSTRACT

Methods for digitizing complex surfaces of dental objects such as impressions of dental surfaces and shapes. While an impression mold is being scanned by translation along a known trajectory, typically in a plane, the line of sight of a distance probe is directed toward successive positions on the surface of the impression mold, such as by a periodic series of reflecting surfaces characterized by normal vectors at distinct non-orthogonal angles with respect to their axis of symmetry. One or more reference objects are scanned using the same translation and mirror positioning systems. Gathered coordinate data are processed to apply angular corrections and combined to form a single distortion-corrected image of the impression mold. An apparatus and methods are provided for measuring both sides of a dental object separately, and then registering the two sides relative to each other in a digital representation of the object.

9 Claims, 8 Drawing Sheets

DOUBLE-SIDED MEASUREMENT OF DENTAL OBJECTS USING AN OPTICAL SCANNER

The present application is a continuation-in-part of U.S. patent application Ser. No. 11/041,520, filed Jan. 25, 2005, and, like that Application, also claims priority from U.S. Provisional Patent Application Ser. No. 60/544,468, filed Feb. 13, 2004. The present application additionally claims priority from U.S. Provisional Patent Applications Ser. Nos. 60/834,138, filed Jul. 28, 2006, and 60/920,972, filed Mar. 30, 2007. All of the foregoing applications are incorporated herein by reference.

FIELD OF THE INVENTION

The present invention relates to the digitization of impressions based on the application of non-contacting metrology, and, more particularly, to methods for optically scanning and digitizing the coordinates of a dental object, such as an impression mold, on one or both sides.

BACKGROUND ART

Recent practice has shown the efficacy, both for diagnostic purposes and for the fabrication of various types of dental appliances, of forming digital images of teeth, or of entire sections of the mouth of a patient. In current practice, digitization is generally performed by scanning actual teeth or by scanning cast models of teeth formed using standard molding and casting techniques.

A dental impression is a negative replica of a given area of the oral cavity. The area replicated may be composed of either hard or soft tissues or both. Dental impressions are typically formed within the mouth of a patient, using an elastic material or a thermo-plastic material, such as a reversible hydrocolloid, that softens above a certain temperature. Other materials used may include various silicone or polysulfide-, and polyether-based synthetic rubber materials. Examples of dental impressions to which the instant invention may advantageously be applied are shown in FIG. 1. Dental impressions are useful for diagnostic purposes and may be used to cast molds, the casted molds being essential in the fabrication of various types of dental appliances, as will be further discussed in the disclosure that follows. In order to cast an accurate copy of teeth or parts of the mouth, plaster or dental stone is typically placed within an impression mold after the mold has been impacted by the patient.

The existing procedures for dental restoration involving the use of dental scanners typically proceeds as follows: First, a tray including an impression mold is inserted into a patient's mouth to create an impression of the patient's teeth and gingival tissue of the upper and lower jaw. The tray is held stationary until the impression material hardens capturing a negative, or reverse image of the teeth and gingival tissue. The tray is then removed from the patient's mouth, retaining the three dimensional impression of the teeth and gingival tissue of both the upper and lower jaw as well as their relative positions.

Following the creation of the impression, two separate plaster (gypsum) models must be produced by poring plaster into the impression mold. Pouring plaster into the impression mold allows separate positive models (top and bottom) of the oral structures to be created. These positive models made from the negative impression mold are referred to as "casts," and, for dental scanners, are generally made from gypsum. The two separate models are held together in a mechanical jig when it is necessary to consider the relative alignment of the upper and lower dental features, as is often the case in dentistry and orthodontia. This process requires skill and is time-consuming.

Coordinate measuring machines (CMMs) are employed to determine the coordinates, in some specified frame of reference, of points on the surface of a workpiece. CMMs may be employed, for example, for digitizing or imaging that may be useful in the process of replicating a prototype for various manufacturing applications. The salient parts of a CMM include a stage, or a series of stages, for moving the object to be characterized, a probe for measuring the distance to a point on the surface of the work piece relative to a fiducial position, a control or computing system, and measurement software for converting the measurements into a meaningful format for the intended application.

One limitation imposed by existing CMMs is that even the most versatile optical sensors are unable to digitize on vertical or very steep angles measured with respect to the optical axis (or 'line of sight') of the probe. 'Vertical', in this case, refers to the surface of the scanned body lying parallel to the optical axis of the probe. An 'undercut' refers to a negative angle relative to the line of sight of the probe. Some applications, however, such as dental surface profiling for purposes of reconstruction, orthodontics, etc., as well as digitization of plastic parts, molds, etc., require measurements on vertical walls or low angle undercuts. Dental impressions, in particular, entail blind holes and sharp angles that are notoriously difficult, if not impossible, to digitize using standard CMM techniques.

As used herein, a body characterized as 'complex' is one having vertical walls or low angle undercuts. The use of prior art technology to scan a complex body requires orthogonal scanning of the object about multiple (typically 5) axis. As used herein, 'orthogonal scanning' refers to scanning of the line of sight of a probe entirely within a single plane normal to an axis of rotation. This method, while algorithmically simple, requires very large travel on the scanning stages making the equipment very expensive.

Another prior art solution to the problem of small (or zero, or negative) angles with respect to the probe line of sight entails performing non-orthogonal scanning by using a 2-axis angular arm. In this case the whole sensor is rotated, and both the complex arm and the requisite large travel ranges add to the cost of such systems. Yet another prior art solution for scanning complex bodies requires changing the sample position to allow direct line of sight for each feature. In this case very complex reconstruction software is required to merge the individual scans by 'best fit' of complex surfaces. The results of the 'stitch' depend on the quality of the data, the size and shape of common features used for references, and the robustness of the algorithms. Typically, operator intervention is required, both during the scanning (otherwise 2 or more motorized axis are required on the sample fixture) and during data processing. In some cases involving dental applications or plastic parts with smooth surface features, it is very difficult to find the right fit and reference items to register successive 'views' of the object. One solution requires 'gluing' registration features ('balls') to the sample.

Dental impressions have not been amenable to digitization for a number of reasons, primary among those reasons being that concave surfaces (and, indeed, abrupt vertical shafts, in some circumstances) are complex, in the sense defined above, prohibiting triangulation scanning processes. Moreover, the translucent optical properties of polymers typically used as impression materials do not provide clear reflecting surfaces and give rise to blurring. Thus, an automated and robust solution to the problem of digitizing complex bodies is acutely desirable as applied to the digitization of impressions, particularly dental impressions.

SUMMARY OF THE INVENTION

In accordance with a preferred embodiment of the present invention, there is provided a method for digitization of impression molds. The method includes but is not limited to the following steps:
a. supporting the impression mold on a stage;
b. translating the impression mold in at least one direction;
c. characterizing distances from the surface of the impression mold to a fiducial reference along periodic sequence of distinct lines of sight; and
d. merging the distances to form an image of the surface of the impression mold.

In accordance with other embodiments of the invention, the distances from the surface may be characterized by varying the lines of sight periodically in a direction parallel to a specified plane while changing concurrently in a direction perpendicular to the specified plane. Moreover, a collinear sensor may be used in the characterization.

Another aspect of the invention may further allow the impression mold to include a negative reproduction of a portion of an oral cavity of a subject. The method of digitization may also include characterizing distances to reference objects of a known shape in conjunction with translation of the impression mold. Each of the characterized distances may be measured, and may be transformed to a common frame of reference. The impression mold may be scanned with a beam and the scanning may be performed in non-coplanar directions.

In another aspect of the current invention, the step of characterizing distances from the surface of the impression mold to a fiducial reference may include measuring distances along a line of sight the elevation of which with respect to a fiducial plane varies periodically with time, and may also include scanning the impression mold with a beam of light reflected from mirrors disposed upon a rotating carousel.

In accordance with yet another aspect of the invention, a method is provided for performing a two-sided measurement of a double-sided impression mold. The method includes but is not limited to the steps of:
a. mounting the impression mold on a holder;
b. measuring a first side of the impression mold and any registration object disposed on the holder;
c. inverting the holder;
d. measuring an opposite side of the impression mold and any registration object; and
e. merging measurements of each side of the impression mold and any registration object to create a merged measurement; and
f. creating a three-dimensional representation of the impression mold by using the merged measurement.

BRIEF DESCRIPTION OF THE DRAWINGS

The foregoing features of the invention will be more readily understood by reference to the following detailed description taken with the accompanying drawings, in which.

DETAILED DESCRIPTION OF SPECIFIC EMBODIMENTS

In preferred embodiments of the present invention, non-contact scanning techniques are employed for the digitization of impression molds, particularly impression molds in soft materials such as those used for dental impressions.

Dental impressions are useful for a variety of purposes including their use as diagnostic tools, their use in defining three dimensional shapes for crowns, bridges, and/or entire implants, as well as their use in various other critical orthodontic procedures. In all of these cases, impression molds are an intermediate stage in the replication of structures within the oral cavity.

The next stage, with which the current invention is particularly concerned, involves the transformation of the impression into a digital format. Time and cost advantages may be obtained by application of the current invention in scanning and transforming the impression mold into a digital format immediately following removal of the mold from the patient's mouth, without the requirement that a positive replica be made via a casting process. This saves labor and materials as well as prevents inconvenience to the patient from having to undergo recurring visits to a dental or orthodontal practitioner, otherwise required when a positive replica needs to be cast.

The non-contact techniques provided in the current invention provide a further advantage in contexts in which the impression mold to be digitized is composed of easily deformed or malleable material because it prevents any incidental or accidental deformation of the impression during the scanning process. In preferred embodiments of the invention, non-contact techniques are applied that are particularly suited to the digitization of complex shapes in translucent media, such as presented by dental impression molds. In particular, X-Y scanning systems may be advantageously combined with a non-contact sensor characterized by an optical axis (or line of sight) and a variable position mirror that varies the line of sight with respect to a scanned body in a manner favorably suited to the automatic digitization of complex bodies such as dental impressions.

Figure 1:
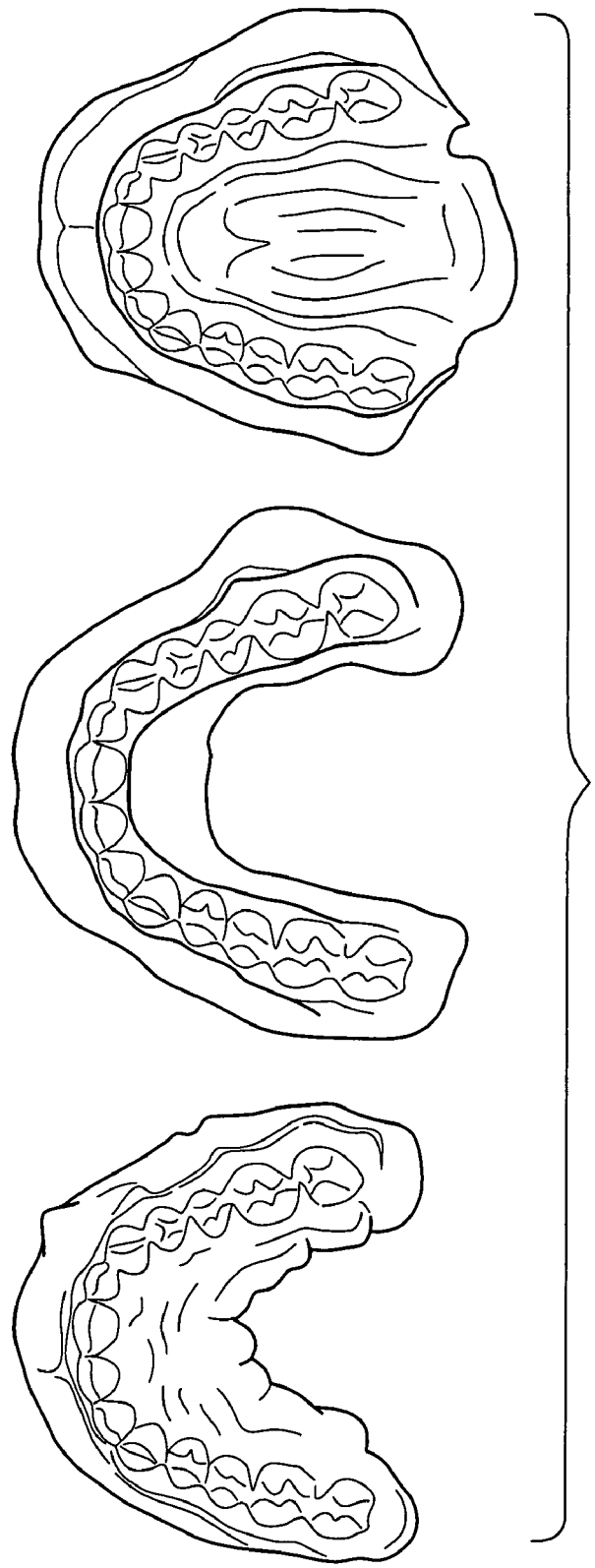
FIG. 1 shows three dental impressions of kinds to which embodiments of the present invention may advantageously be applied.
Figure 2:
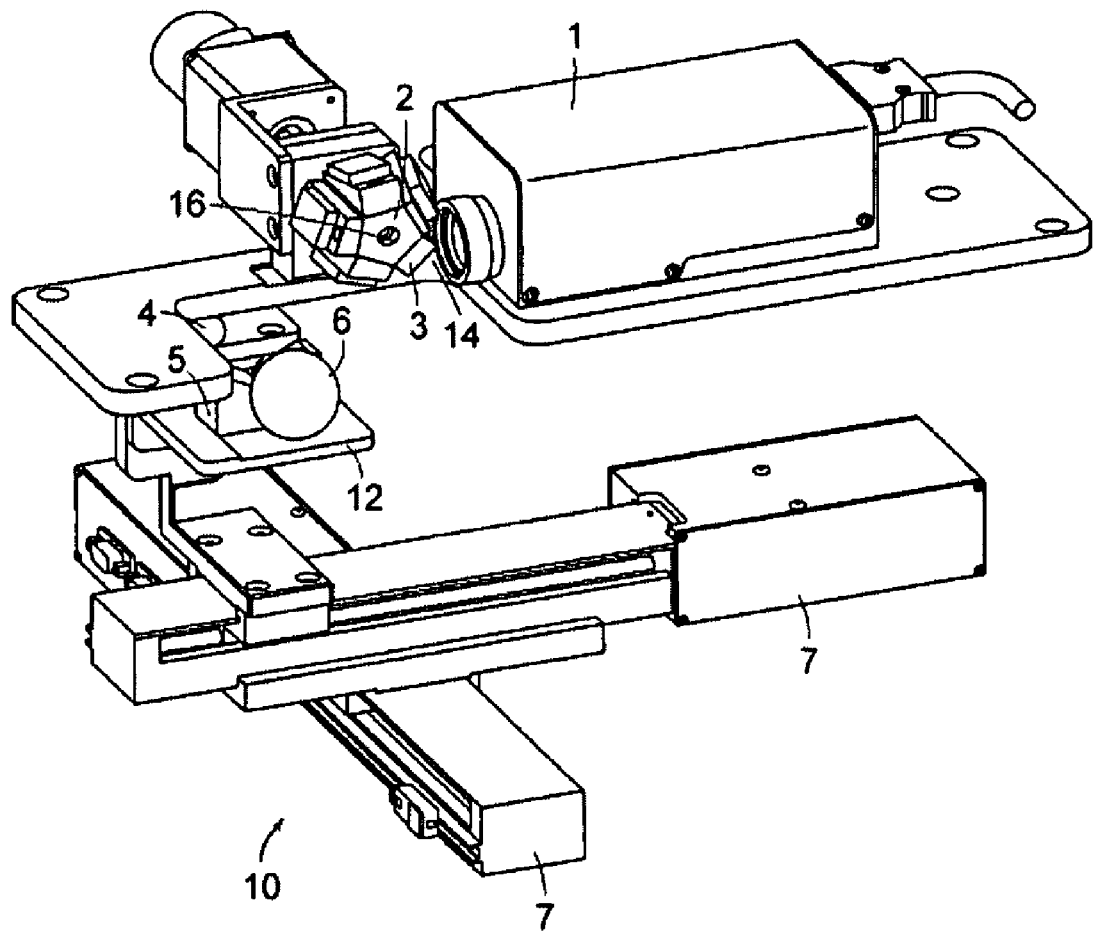
FIG. 2 is a cutaway view of a multiple angle scanning system depicting the scanning of a spherical object in accordance with an embodiment of the present invention.

Referring, first, to FIG. 2, a perspective view is shown of the salient components of a scanning system in accordance with preferred embodiments of the present invention. The impression mold to be measured (which may be referred to generally, herein, as the "object" or the "body"), is represented in FIG. 2 by a sphere 6 disposed on carriage 12 of coordinate measuring machine 10. Reference bodies may also be disposed on carriage 12 (also referred to as a 'support') so as to travel in synchronization with object 6 as the object is translated by the carriage. Two reference bodies are shown in FIG. 2: a reference sphere 4 and an angular reference V prism 5. However, it should be understood that more or less reference bodies may be provided in the same or in a different form, and, in preferred embodiments of the invention, four reference spheres are employed. Carriage 12 may be translated, along the orthogonal axis, through the motion of orthogonal X-Y translation stages 7; however, all means of translating object 6 during the course of scanning are within the scope of the present invention. Other means of moving carriage 12 along a known trajectory include but are not limited to motion along a vertical (Z) axis and rotation about one or more specified axis.

A distance probe 1 is typically characterized by an optical axis or line of sight, designated, in FIG. 2, by the line denoted by numeral 14. In preferred embodiments of the invention, a laser beam is emitted collinearly with optical axis 14 of distance probe 1. Distance probe 1 is a non-contact sensor such as a conoscopic sensor, or any other distance probe. A conoscopic sensor is preferred, as discussed below, since it uniquely provides for the digitization of blind holes and sharp angles.

Figure 8:
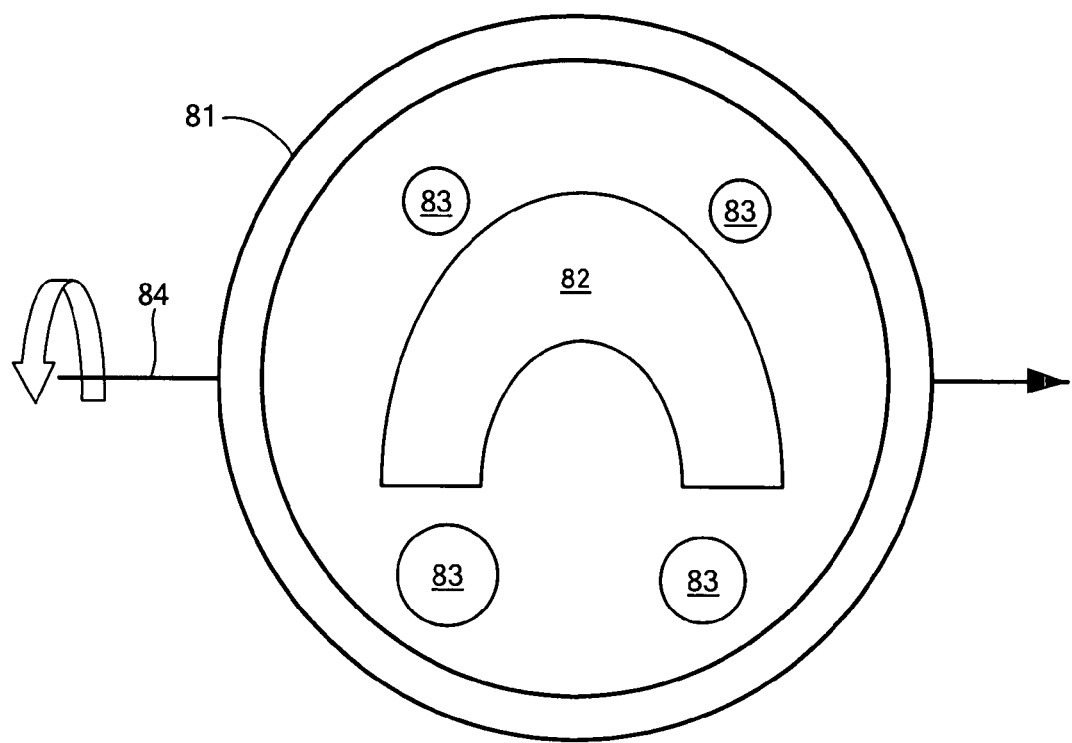
FIG. 8 is a depiction of a holder for retaining an object and one or more reference objects for dual-sided scanning in accordance with embodiments of the present invention.

Various aspects of the invention, including holder 81 shown in FIG. 8, are optimized for measuring impressions (or other objects, dental or otherwise) through the use of optical scanners that employ sensors based on conoscopic holography or other collinear optical sensors. A collinear sensor is a sensor in which the optical axis of the light emitted from the sensor coincides with the optical axis of the light that is returned to, and collected by, the sensor.

Various probes may be employed for measuring a distance to the surface of the measured work piece. Any probe, currently known or otherwise, is within the scope of the present invention, although, in an embodiment preferred for reasons discussed below, a particular form of probe is employed that is typified by the ConoProbe™ supplied by Optimet, Optical Metrology Ltd. of Jerusalem, Israel. The preferred probe employs conoscopy, a form of holography. Conoscopy is an interferometric technique capable of determining the distance to one or more points on an object surface without employing a reference beam. Instead, light emanating from a source region is prepared in a defined state of polarization and then passed through an anisotropic optical element in which one polarization suffers phase retardation with respect to the other. The two polarization components emerging from the anisotropic optical element interfere with one another, producing an interferogram in the detector plane. Conoscopy is the subject of various patents, including U.S. Pat. Nos. 4,602,844, 4,976,504, 5,081,540, 5,081,541, and 5,953,137, all of which patents are incorporated herein by reference.

In accordance with embodiments of the invention, a line of sight 14, and the laser beam coaligned with it, is bent by one or more folding mirrors 3 so that the line of sight impinges upon the surface of the impression mold to be scanned, represented by object 6. It is to be understood that the optical path shown is described for purposes of convenience and that more complex optical paths, entailing any other optical elements, are within the scope of the present invention as described herein and as claimed in any appended claims.

In accordance with preferred embodiments of the invention, a plurality of folding mirrors 3 are mounted on a multi-position actuator 2 in a manner that allows laser beam bending in different directions. Multi-position actuator 2 may be a carousel supporting multiple mirrors that is rotated about a central axis 16. More particularly, mirrors 3 may be mounted on a polygon, such as the pentagon shown in FIG. 2. Mirrors 3 may be reflecting surfaces fashioned in the carousel in a continuous or discontinuous sequence of normal directions. The mirrors may also be mounted in preset positions, as shown in FIG. 2. The normal directions of successive reflecting surfaces are disposed at varying angles with respect to the plane normal to the axis of rotation of multi-position actuator 2. Thus, as the actuator is rotated, the line of sight of the distance probe does not sweep out a plane but varies over a range of elevation angles, typically on the order of ±20° with respect to the orthogonal plane, or to some other fiducial plane. This variation is periodic, in that it repeats each rotation of the carousel.

Measurements of distances to the surface of body 6 along line of sight 14 are collected and processed separately for each of the mirrors 3, thus forming a distinct 'cloud' of points attributable to that mirror. Merger (or 'stitching') of the respective clouds of points to form a single consistent image is discussed below. Conoscopy is a preferred method for measuring the distance to the surface of a translucent body, a characteristic that is typical of the material from which a dental impression is formed, because conoscopy allows resolution of a blurred return that might result due to light scattered within the translucent material rather than light reflected at the surface.

In the case where mirrors 3 are disposed at preset angles, after assembly, an accurate measurement of each bending angle is performed for each position of the actuator. The measured angle values are transferred to the software and used for the coordinate transformation from a coordinate system based on motion of the scanning system 7 to an orthogonal coordinate system. (Since the line of sight is incident onto the surface of the object at an angle that is specific to each mirror position, a separate coordinate system attaches to each position of the mirror until coordinates are transformed to an orthogonal system.)

Desired bending angles may be calculated for a particular application in order to cover the desired undercut angle and leave enough working range. Mirrors 3 may then be adjusted and set accordingly. High bending angles will reduce the actual working range relative to the vertical position, thus requiring a larger range of travel for the moving stages.

It is to be noted that the main scanning movement (typically X-Y) may be performed either by the measured object and reference samples fixed on a mounting table or, as a matter of design choice, by the sensor mounted together with the folding mirrors on a common support. Both equivalent motions are within the scope of the present invention.

Data from the measurements described herein is advantageously gathered and processed automatically without human intervention. In order to increase accuracy of measurement, a fixed reference object (sphere 4, V prism 5) is scanned before the part is scanned, enabling an accurate evaluation of the beam position relative to the X-Y scanning system 7.

All the gathered data for each mirror position is processed by first applying the angular correction for the profiles to orthogonal coordinates and then shifting the origin using the spherical fit to translate the local coordinates to the same origin in a frame of reference fixed with respect to the body. Since the measured object 6 remains fixed (relative to the mounting device, carriage 12) for the entire measurement cycle, the actual X, Y coordinates of each point are the same for all beam positions, thus simple robust mathematical methods are advantageously employed for data processing in a totally automatic cycle.

Figure 3:
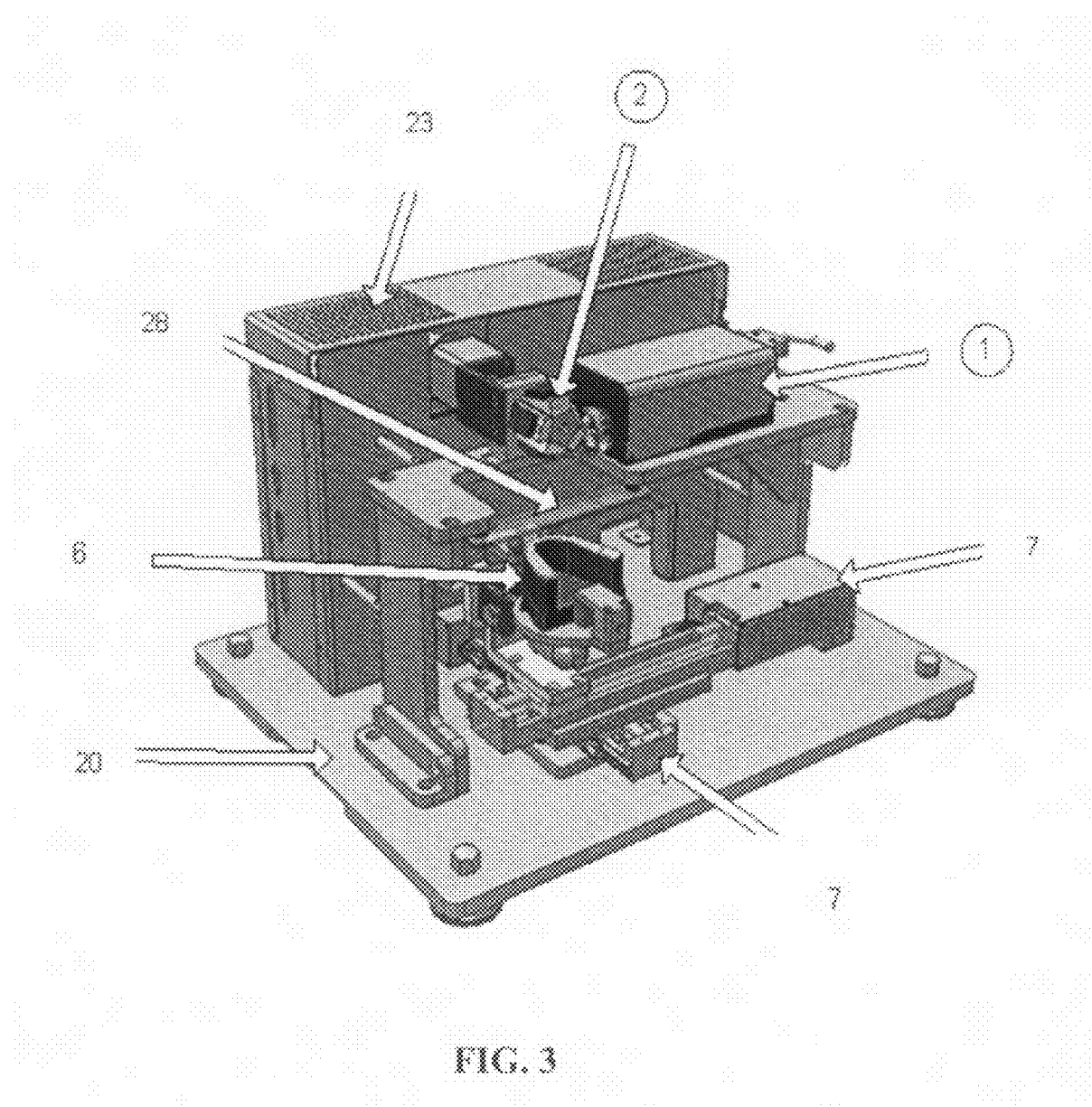
FIG. 3 is a perspective view of a multiple angle scanning system for dental applications, in accordance with a further embodiment of the present invention.

Referring now to FIG. 3, a coordinate measuring machine employing an embodiment of the present invention is shown, with components labeled as described above with reference to FIG. 2. The scanned object 6 in this illustration is a dental mold. It is to be understood that object 6 may be referred to herein as a "dental object," without restricting the general scope of the invention. Also shown are base 20 and controller box 23 containing a processor for control of motion of stage actuators 7 and analysis of clouds of points from each mirror position and merger of the separate clouds into one single cloud that reflects the actual shape of the 3D object.

The apparatus and methods described herein are advantageously applied to collinear, non-contact measurement sensors that require simple, trigonometric based transformation algorithms. A complete or partial reconstruction of a 3D object may be derived. For example, 360 degrees of a sphere may be reconstructed with a 3-axis X, Y, Z/rotating axis and one axis mirror drive or X-Y system and 2 axis mirror drive or 270 degrees of a sphere may be reconstructed with a 2 axis X-Y and one axis mirror drive.

In accordance with alternate embodiments of the invention, non-orthogonal scanning with a non contact sensor may be applied to common X-Y CMM scanning machines, with optional Z translation or rotation about specified axes.

Figure 4A:
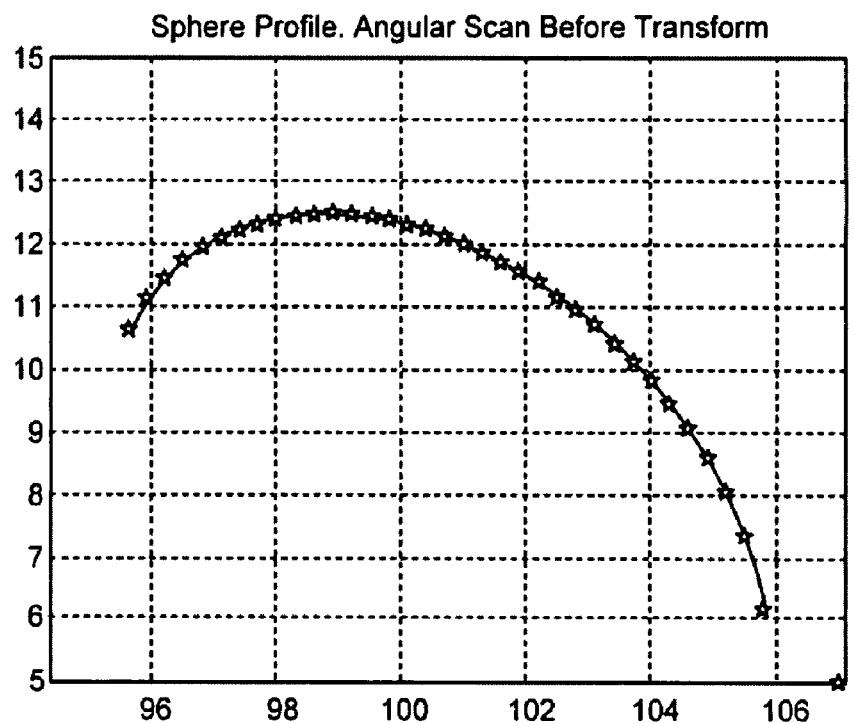
FIG. 4A shows a circular profile (sphere/cylinder) as measured in non orthogonal coordinates (laser beam bent normal to main scanning direction) and FIG. 4B shows the profile of FIG. 3A after transformation to orthogonal coordinates.
Figure 4B:
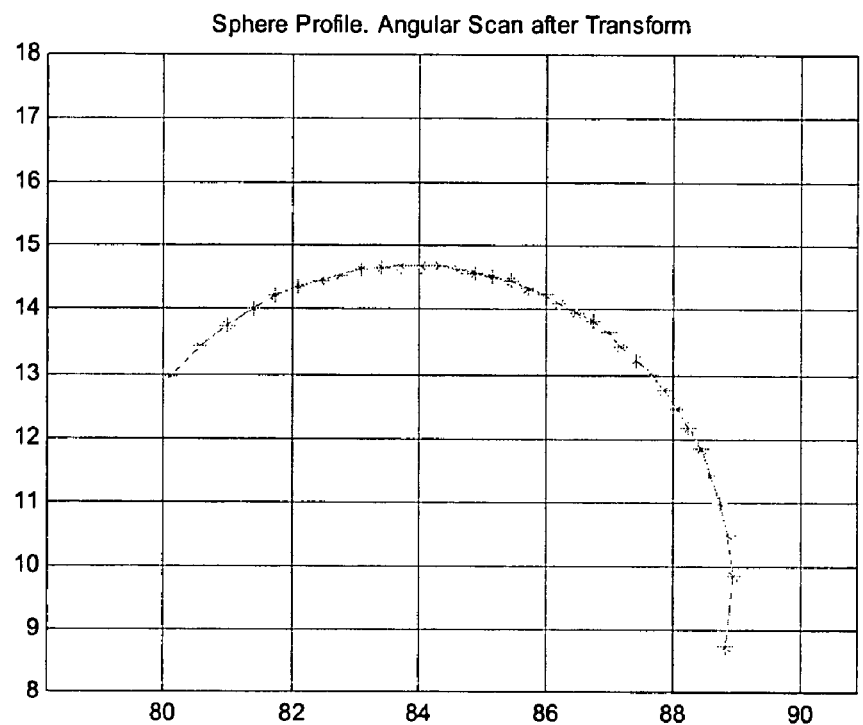

After the setup in which sample borders are defined in the software, data gathering proceeds automatically. Trigonometric matrix transformations of the non-orthogonal coordinates and a sphere fit provide for relative coordinate origin translation, transforming the raw data of FIG. 4A to the spherical fit of FIG. 4B.

Figure 5:
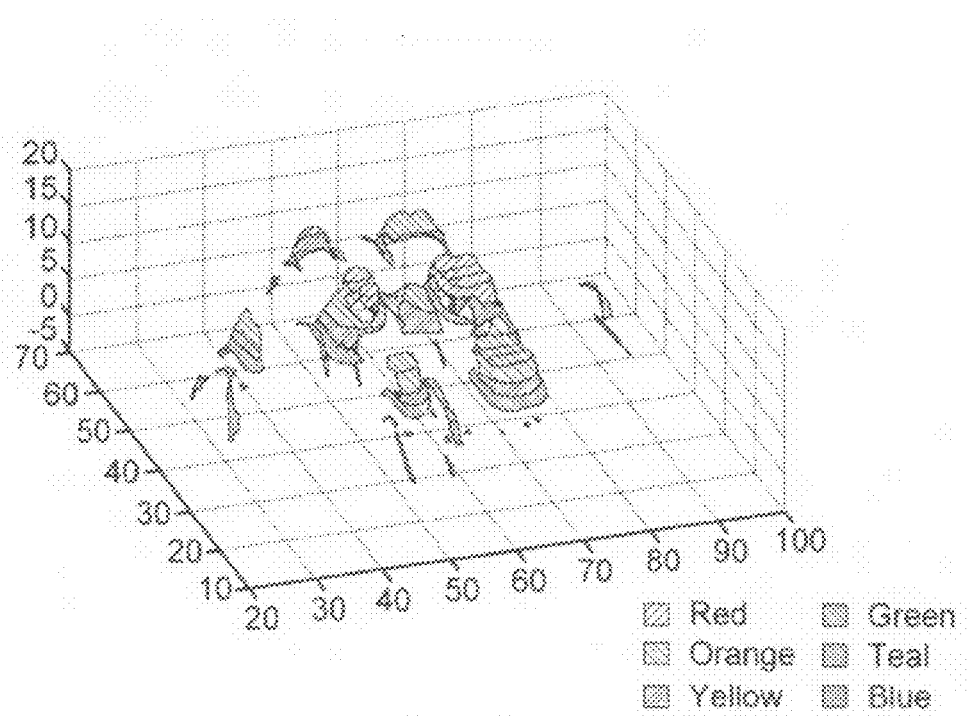
FIG. 5 shows an image derived from 5 different surface scans taken with 5 mirror positions after profile reconstruction in accordance with embodiments of the present invention.
Figure 6:
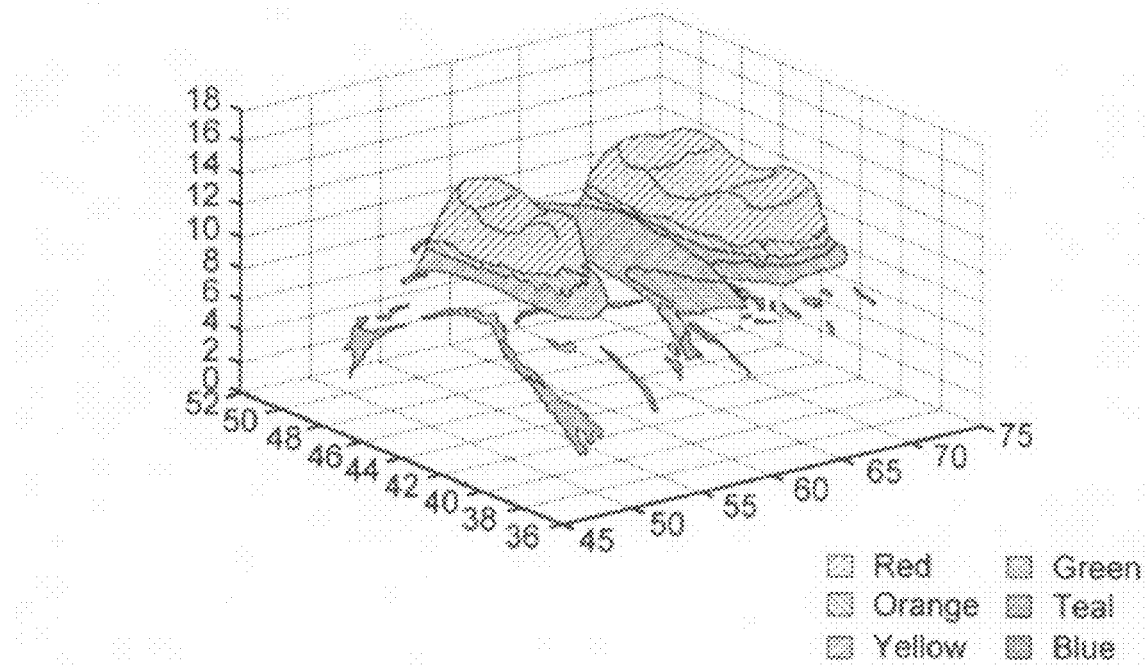
FIG. 6 is a depiction of the scans shown in FIG. 5 after coordinate translation, using a fit of the reference sphere for the translation.
Figure 7:
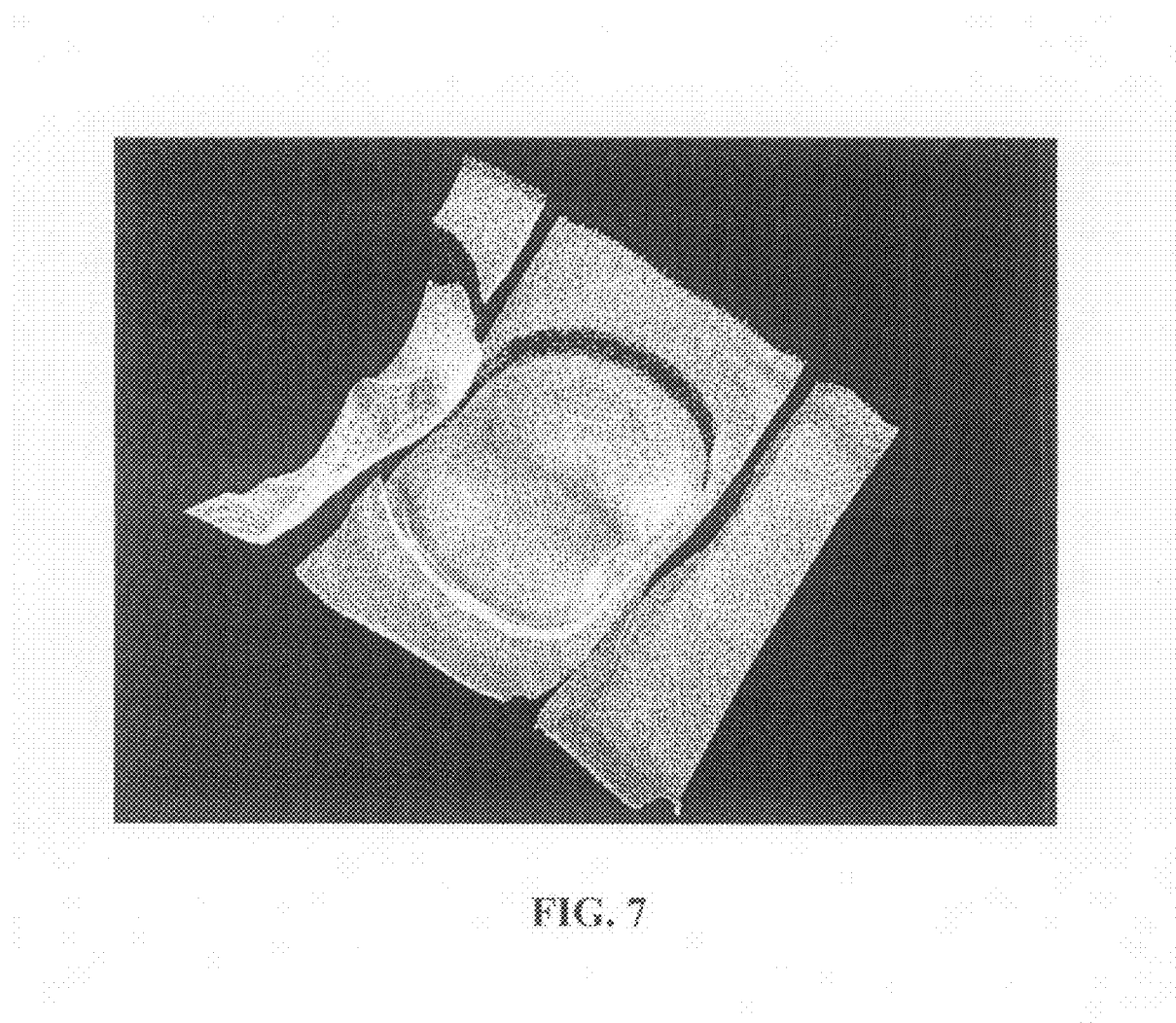
FIG. 7 is a depiction of the scans shown in FIG. 5 after coordinates translation using sphere fit (of the reference sphere) for the translation.

Point clouds due to distinct partial scans, as shown in FIG. 5, may be merged, after coordinate transformation and translation to the merged point cloud shown in FIG. 6.

In a variety of applications, it is advantageous to record and register both sides of a dental impression, or of other dental objects. The impression may include information on the relative position of the upper and lower teeth, an important parameter for various dental restoration procedures.

In accordance with embodiments of the present invention, a procedure and apparatus are provided for measuring both sides of a dental impression separately by a non contact optical scanner. Scanning of each side provides a partial digital representation, which is then typically recorded, and the two partial digital representations are registered relative to each other in order to derive a complete three-dimensional model of the structure of which the impression mold is a negative replica.

To that end, and in accordance with further embodiments of the present invention, as depicted in FIG. 8, a mechanical mount (also referred to, herein as a "holder") 81 is disposed on a non contact optical scanner (shown in FIG. 3, for example) and employed in conjunction with a mathematical registration and localization algorithm as now described. The impression or other object 82 (which, most generally, is not limited to dental objects) is mounted on the holder 81. The object 82 is measured from both sides separately, in accordance with procedures described above. The separate scans are then merged mathematically, using 3-D information based on reference objects 83 that are disposed on either side of holder 81 at known positions. The result of this procedure is the production of 3-D information of a double sided dental impression.

FIG. 8 shows the mechanical holder 81 adapted to mount double-sided impressions or dental objects 82. The holder includes alignment mechanisms to adjust the angle of the object following simplified procedures. The holder 81 is double sided and can be flipped about axis 84 in order to measure separately and sequentially the impression of the upper and lower jaw.

One or several three-dimensional registration objects 83 are provided on holder 81. The 3D registration objects may be spheres and/or pyramids, for example. Four spheres are preferably used. The registration objects 83 may also be mounted in such a manner as to be visible on both sides of the holder 81. The registration objects 83 may be mounted on the holder, or, alternatively or additionally, on the dental object 82 itself. The registration objects can differ in size, shape or disposition on the holder 81.

Figure 9:
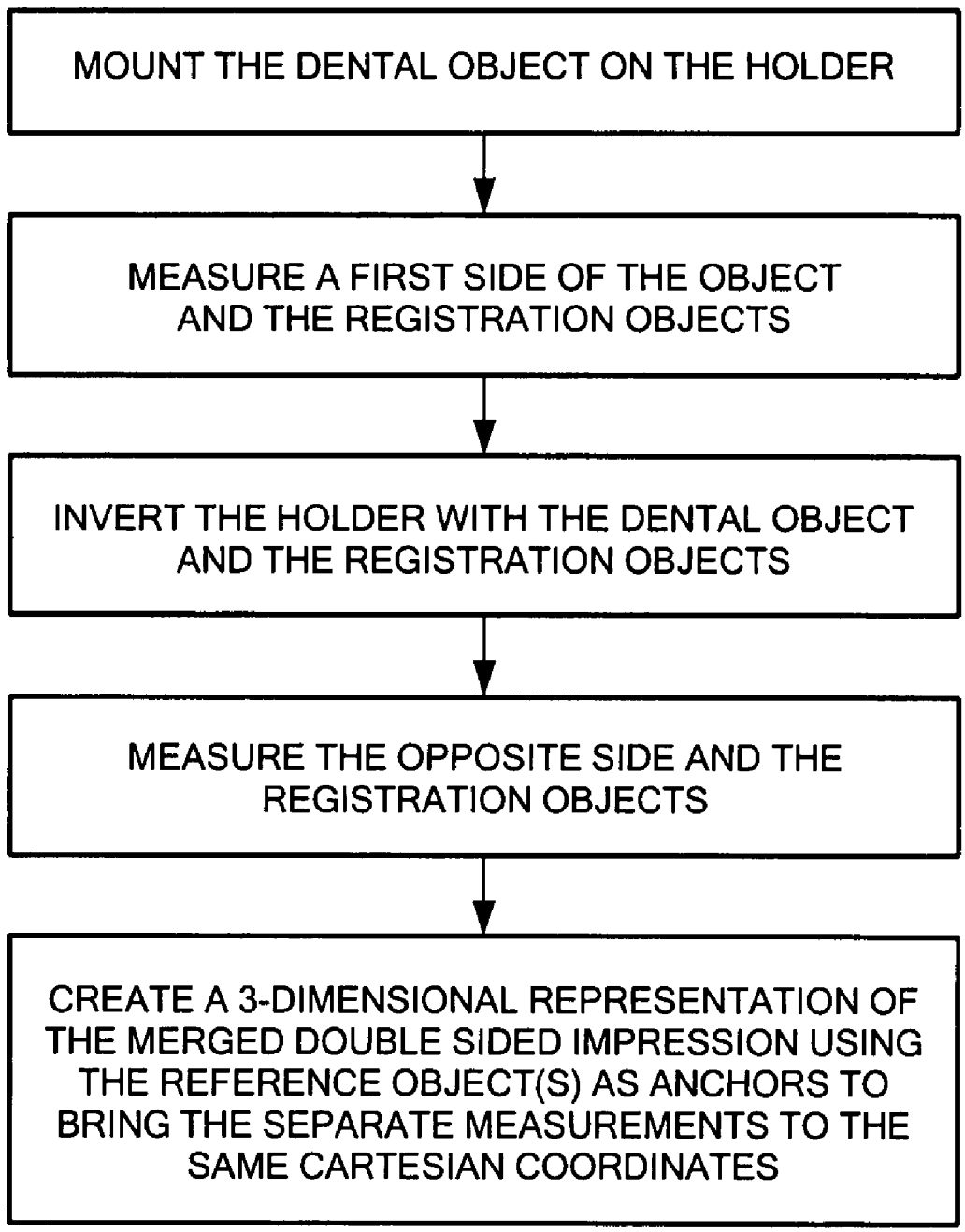
FIG. 9 is a flowchart depicting the steps of a method for measuring a dental object and registering measurements performed on each of two sides in accordance with embodiments of the present invention.

A method for performing a two-sided measurement, in accordance with embodiments of the invention, is depicted in the flowchart of FIG. 9. The measurement procedure includes Mounting the dental, or other, object on the holder.

Measuring the upper or the lower side of the object and the registration objects.

Inverting the holder with the dental object and the registration objects.

Measuring the opposite side and the registration objects.

Creating a three-dimensional representation of the merged double sided impression by using the exact positions of the reference objects as anchors and applying mathematical procedures, as discussed above, for example, to bring the separate measurements to the same Cartesian coordinates.

The described embodiments of the inventions are intended to be merely exemplary and numerous variations and modifications will be apparent to those skilled in the art. All such variations and modifications are intended to be within the scope of the present invention as defined in the appended claims.

What is claimed is:

1. A method for digitizing an impression mold, the impression mold characterized by a surface, the method comprising:
   a. supporting the impression mold on a stage;
   b. translating the impression mold in at least one direction;
   c. characterizing a plurality of distances from the surface of the impression mold to a fiducial reference along a periodic sequence of distinct lines of sight;
   d. measuring a plurality of distances to a reference object of known shape during a course of translation of the impression mold;
   e. transforming the plurality of distances to the reference object to a common frame of reference; and
   f. merging the plurality of distances from the surface of the impression mold to the fiducial reference to form an image of the impression mold.

2. A method according to claim 1, wherein the step of characterizing further includes:
   varying the lines of sight periodically in a direction parallel to a specified plane while changing concurrently in a direction perpendicular to the specified plane.

3. A method according to claim 1, wherein the step of characterizing further includes using a collinear sensor.

4. A method according to claim 1, wherein the impression mold includes a negative reproduction of a portion of an oral cavity of a subject.

5. A method according to claim 1, further comprising:
scanning the impression mold with a beam of light.

6. A method according to claim 5, wherein the step of scanning includes scanning the beam of light in non-coplanar directions.

7. A method according to claim 1, wherein characterizing the distances from the surface of the impression mold to a fiducial reference includes measuring the distances along a line of sight the elevation angle of which with respect to a fiducial plane varies periodically with time.

8. A method according to claim 7, wherein characterizing distances further comprises:
scanning the impression mold with a beam of light reflected from mirrors disposed upon a rotating carousel.

9. A method according to claim 1, the method further comprising:
c. inverting a holder supporting the impression mold;
d. measuring an opposite side of the impression mold and the reference object; and
e. merging measurements of each side of the impression mold and the reference object to create a merged measurement; and
f. creating a three-dimensional representation of the impression mold by using the merged measurement.

* * * * *